United States Patent [19]

King

[11] Patent Number: 5,894,840
[45] Date of Patent: Apr. 20, 1999

[54] ENDOTRACHEAL TUBE HOLDER

[76] Inventor: George Hwa Kou King, 30452 Via Rivera, Rancho Palos Verdes, Calif. 90275

[21] Appl. No.: 08/567,239

[22] Filed: Dec. 5, 1995

[51] Int. Cl.⁶ ..................................................... A61M 16/00
[52] U.S. Cl. ........................... 128/200.26; 128/206.29; 128/207.17; 128/DIG. 26
[58] Field of Search .................... 128/200.26, 207.14, 128/DIG. 26, 912, 207.17, 206.29

[56] References Cited

U.S. PATENT DOCUMENTS

| | | | |
|---|---|---|---|
| 3,774,616 | 11/1973 | White et al. | 128/200.26 |
| 4,516,293 | 5/1985 | Beran | 128/207.17 |
| 4,744,358 | 5/1988 | McGinnis | 128/207.17 |
| 4,896,667 | 1/1990 | Magnuson et al. | 128/207.17 |
| 5,069,206 | 12/1991 | Crosbie | 128/207.17 |
| 5,395,343 | 3/1995 | Iscovich | 128/DIG. 26 |
| 5,546,938 | 8/1996 | McKenzie | 128/207.17 |

*Primary Examiner*—Aaron J. Lewis
*Attorney, Agent, or Firm*—David and Raymond; Raymond Y. Chan

[57] ABSTRACT

An endotracheal tube holder with integrated bite-block includes a holding element for holding the endotracheal tube holder in patient's mouth position, a tube securing element protruded on one side of the holding element for securing an endotracheal tube thereto, and an intra-oral means which is a bite block for inserting into the mouth of the patient to prevent the endotracheal tube being bitten by the patient. The endotracheal tube holder is designed for dual function of fast and firm securing the endotracheal tube as well as protecting the endotracheal tube from movement, dislodgment and being bitten, in order to ensure the patient's airway during surgery as well as in postoperative or other intensive care units, or in any situation where patient's airway needs to be secured or protected.

2 Claims, 7 Drawing Sheets

ENDOTRACHEAL TUBE HOLDER

BACKGROUND OF THE INVENTION

The present invention relates to the safety of endotracheal intubation in patient airway management, and more particularly to a dual function endotracheal tube holder which is employed in securing an endotracheal tube and protecting it from movement, dislodgement and being bitten by the patient, hence to ensure the patient's airway during surgery as well as in postoperative or other intensive care units/ areas, or in any situation where patient's airway needs to be secured or protected. Employing the present invention will prevent all above mentioned complications which can be life-threatening or fatal.

Endotracheal intubation, placement of a tube into the trachea, is an integral part of airway management in modern-day medical practice. It plays a vital role and has the first priority in unconscious patients, patients under or emerging from general anesthesia, victims require acute resuscitation, and various patients need chronic or critical intensive medical care. Endotracheal intubation is the most rapid and usually the easiest method to ensure a patent airway. It has, therefore, earned its popularity in anesthesia practice as well as in emergency medicine and intensive care units/areas. The advantages of endotracheal intubation are many. Since patency of the airway is assured, aspiration is prevented and secretions may be removed with relative ease from the tracheobronchial tree. Positive pressure ventilation, either manual or mechanical, can be applied to the airway for better control of ventilation and oxygen supply.

However, endotracheal intubation does not guarantee a patent airway. The endotracheal tube may be kinked, dislodged, or accidently extubated or being bitten by the patient, particularly when the patient is semiconscious and not paralyzed. The situations are usually fatal particularly when a wire reinforced endotracheal tube is used. A wire reinforced endotracheal tube is generally employed due to concern that external pressure or the head/neck position may compress the airway. A distorted airway may be difficult to re-intubate. A reinforced endotracheal tube will maintain its shape better than a plastic non-reinforced one. However, once the metal in a reinforced tube has been bent out of shape, it remains pinched or collapsed, which leaves the patient in a more dangerous predicament.

After intubation, patient's airway is reasonably secured but not guaranteed. Failure to fasten an endotracheal tube properly may cause dislodgment or displacement of the tube, or even accidental extubation. These complications usually are life- threatening or even fatal. Continued improvement in equipment have prevented many of the associated complications. Nonetheless, tube collapse/ occlusion by patient's biting are still the main unsolved problem. However, they can be avoid or eliminated by equipment design.

Currently, a Guedel oral airway, a curved device to be inserted into the mouth, as shown in FIG. 5, is employed to prevent patient's biting. As shown in FIG. 6, an endotracheal tube is conventionally secured employing adhesive tape together with a Guedel oral airway. Shortcomings in this method are that this oral airway may fail to serve its purpose as a bite-block. Since only the short distal straight portion of the modern plastic disposable oral airway is firm enough to prevent biting and due to its curvature the oral airway can only be placed in the midline. When the patient is semiconscious but not paralysed, he or she may be able to use the tongue to push the oral airway out and bite on its soft portion as well as on the endotracheal tube. The patient can also push the endotracheal tube between the molars and bite on it. Futhermore, when an over-sized oral airway is used, the patient may not be avle to tolerate such an aid. Additionally, it can even cause airway obstruction by its very presence. Prolonged or improper use of oral airway can cause trauma and infection of oropharyngeal tissues, and subsequently increase hospital days and costs.

As shown in FIG. 6, the conventional Guedel oral airway described above is generally secured with adhesive tape to the patient's mouth that the adhesion of the Guedel oral airway in proper position can not last long. Especially, to some patients who have beard or have oily or hairy skin, the tape adhesion is unreliable and may cause danger to the patients.

The introduction of the present invention as described herein will eliminated all these problems. The herein described invention has a great promise as a major advancement in airway management which plays a vital role in modern medicine.

SUMMARY OF THE INVENTION

The main object of the present invention is to provide an endotracheal tube holder which can firmly and effectively fasten the endotracheal tube to the patient and thus prevent movement, malposition, dislodgment, and accidental extubation by the patient during perioperative periods, in emergency or intensive units, or any situation where patient's airway needs to be secured or protected.

Another object of the present invention is to provide an endotracheal tube holder which comprises a bite-block of effective small size for not only to prevent the endotracheal tube from occlusion or obstruction due to patient's biting on the tube, but also to facilitate intra-oral maneuvers/ procedures. Due to its miniature size that also minimnizes the risks of trauma and subsequently infection to the oropharyngeal tissues. This feature is of particular value to those patients at various intensive care units as they generally need to be intubated for prolong periods.

Another object of the present invention is to provide an endotracheal tube holder which enables a fast and easy operation of fastening the endotracheal tube to the patient. The small transparent holding wing(s) of the device provides additional value in maxillofacial surgery where the facial relationships shall be visualized to allow correct repositioning of the malpositioned segments.

Another object of the present invention is to provide an endotracheal tube holder in which the usage of the conventional adhesive tapes that are currently generally used to secure the tube can be confined to a narrow area or be eliminated at all.

Accordingly, the endotracheal tube holder of the present invention, made of non-toxic plastic material, is an one-time use disposable device and comprises an adhesive backed plate-form holding element made of resilient plastic material for fastening the device to the patient, a tube securing element extended from one side of the central portion of the holding element for securing an endotracheal tube to the device, and an elongated intra-oral means on the opposite side of the holding element for inserting into the patient's mouth to protect the endotracheal tube from being bitten by the patient. In accordance with a preferred embodiment of the present invention, the intra-oral means is a bite-block which is a prolonged firm plastic limb with a tube recess aligned longitudinally with the tube securing element. The holding elements can be in different shapes and sizes, all have holding holes on their outer sides for connecting to a fastening tape or even surgical sutures to meet the needs of different clinical situations. This endotracheal tube holder/bite-block combination device can be manufactured in different sizes to adapt different patient sizes from new born to adult.

Endotracheal tube secured by the present invention is much safer than the current technique of using adhesive tapes which may lose its holding ability, particularly when get wet either due to patient's secretion or sweat. The function of the bite-block is to prevent patient's biting on the endotracheal tube and cause obstruction (suffocation). Due to its firm quality, straight shape, and as it is closely secured to the endotracheal tube, the endotracheal tube can be protected from patient's biting in any clinical situation. Additionally, due to its miniature size it will not irritate and/or traumatize the oropharyngeal tissues.

DETAILED DESCRIPTION OF THE INVENTION

Figure 1:
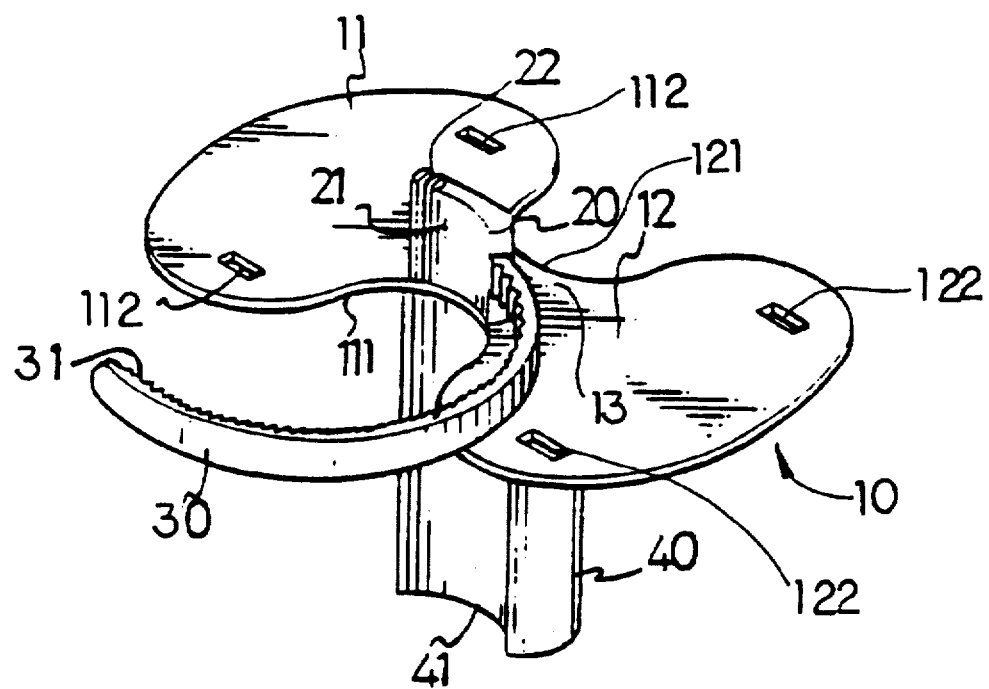
FIG. 1 is a perspective view of a preferred embodiment according to the present invention.

Referring to FIGS. 1 to 4 and more specifically to FIG. 1, a disposable dual function endotracheal tube holder with integrated bite-block, made of non-toxic plastic material, comprises a plate-form holding element 10 made of non-toxic resilient plastic material as fastening means to the patient in order to ensure the endotracheal tube holder in its operating position, a tube securing element 20 disposed on one side of the holding element 10 for securing an endotracheal tube 70 thereto, and an intra-oral means 40 connected to the another side of the holding element 10 opposing the tube securing element 20 for inserting into the patient's mouth to prevent patient's biting of the endotracheal tube 70 (as shown in FIG. 2).

The holding element 10, which is adhesive backed with non-allergic material and positioned between the tube securing element 20 and the intra-oral means 40, has one or two pieces of holding wings 11, 12 with enlarged circular disc shape and a central neck 13. According to the present embodiment, the two holding wings 11, 12 are adhesive backed with non-allergic material and are integrally connected to one or both ends of the central neck 13. So that the two transverse side edges of the neck 13 form two opposing concave curvatures 111, 121 respectively to facilitate intra-oral observation, manipulation or suctioning (as shown in FIG. 2). Each holding wing 11, 12 has two holding holes 112, 122 respectively formed on their two opposing outer sides.

In accordance with the present invention, the tube securing element 20 is a protrusion of predetermined height which is integrally and perpendicularly protruded from one side of the neck 13 of the holding element 10. The intra-oral means 40 is an elongated bite-block extended from other side of the holding element 10 and is aligned longitudinally with the tube securing element 20. The bite-block 40, which is a prolonged non-toxic plastic limb, as well as the holding element 10 and the tube securing element 20 have predetermined sizes respectively adapted to various patient mouth sizes, from newborn to adult patients.

Figure 2A:
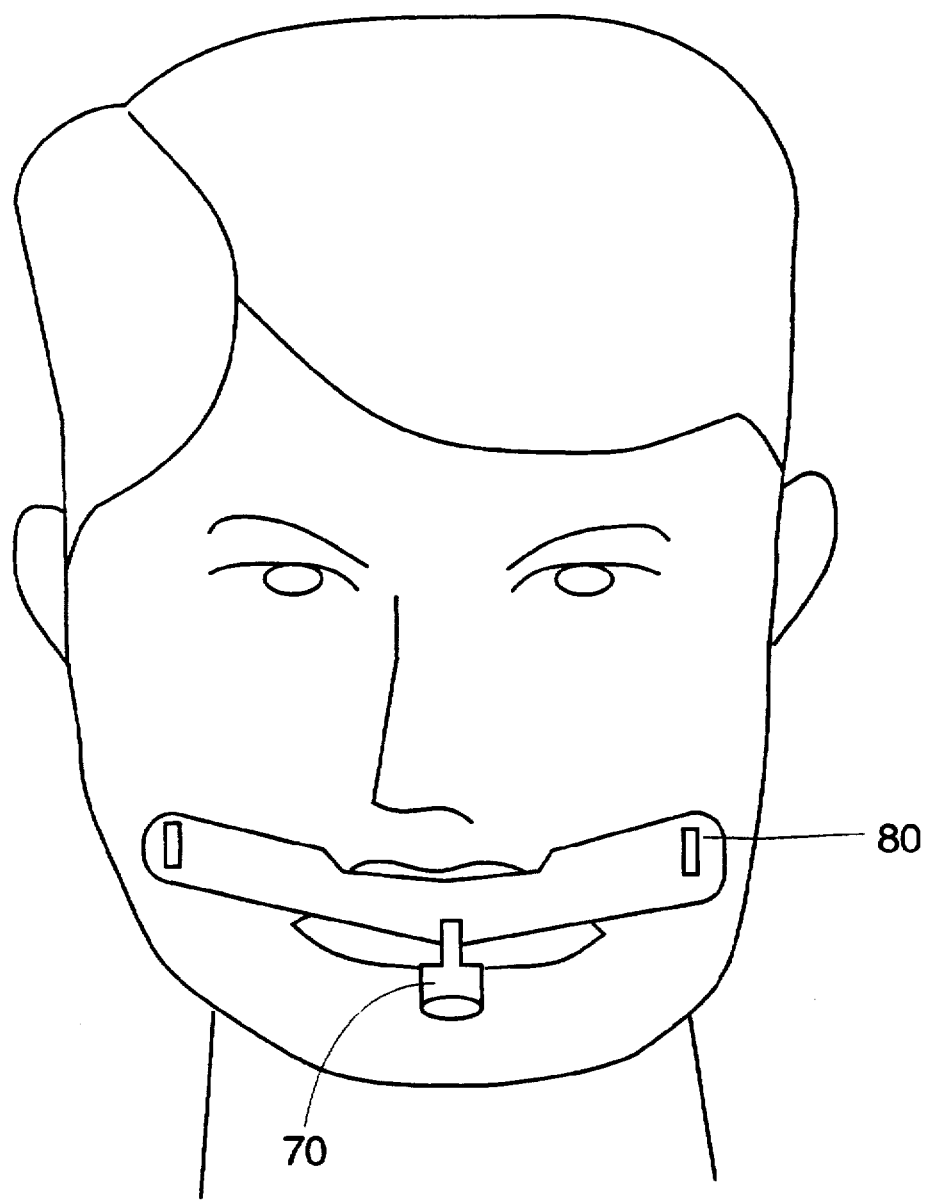
FIGS. 2A and 2B are the plan views of the above preferred embodiment applied on patients with an I-shaped strap and a double Y-ended strap respectively according to the present invention.
Figure 2B:
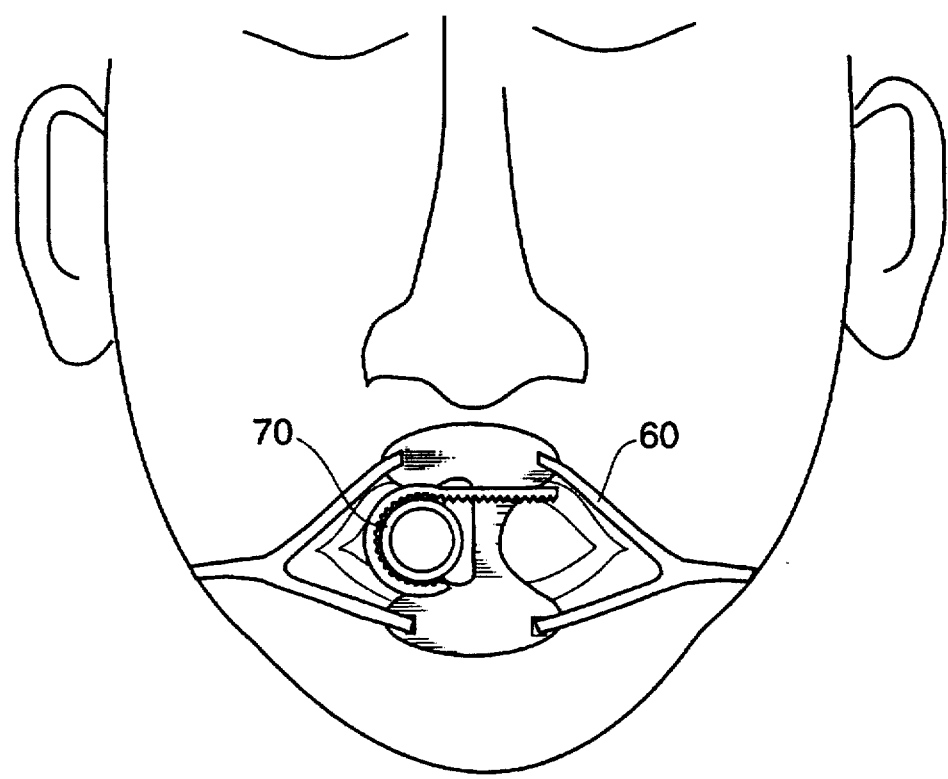
Figure 4A:
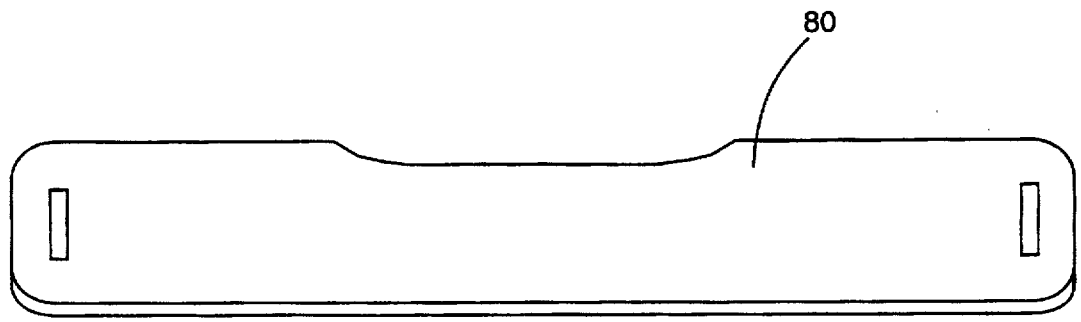
FIGS. 4A and 4B are plane views of various holding devices which can be equipped with the above embodiment according to the present invention.
Figure 4B:
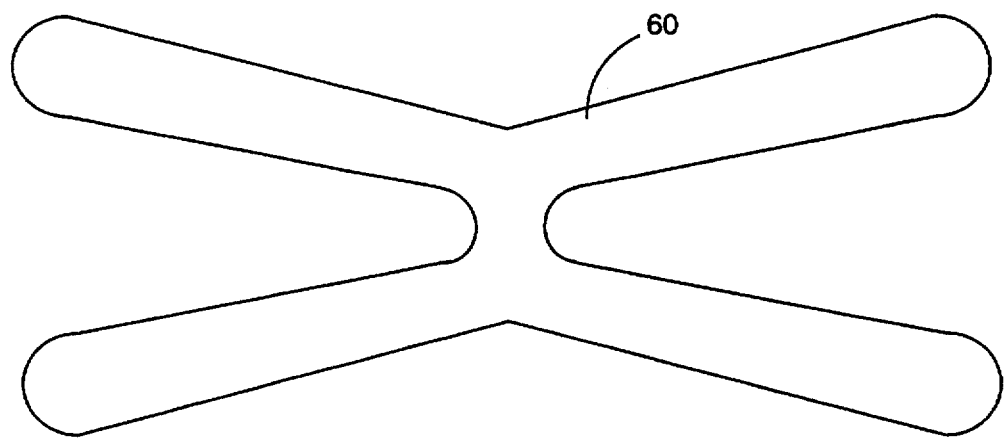
Figure 5:
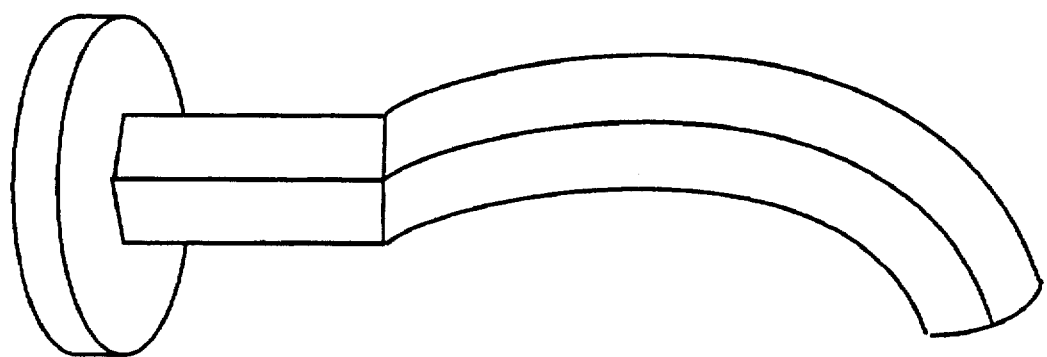
FIG. 5 is a plan view of a conventional Guedel oral airway.
Figure 6:
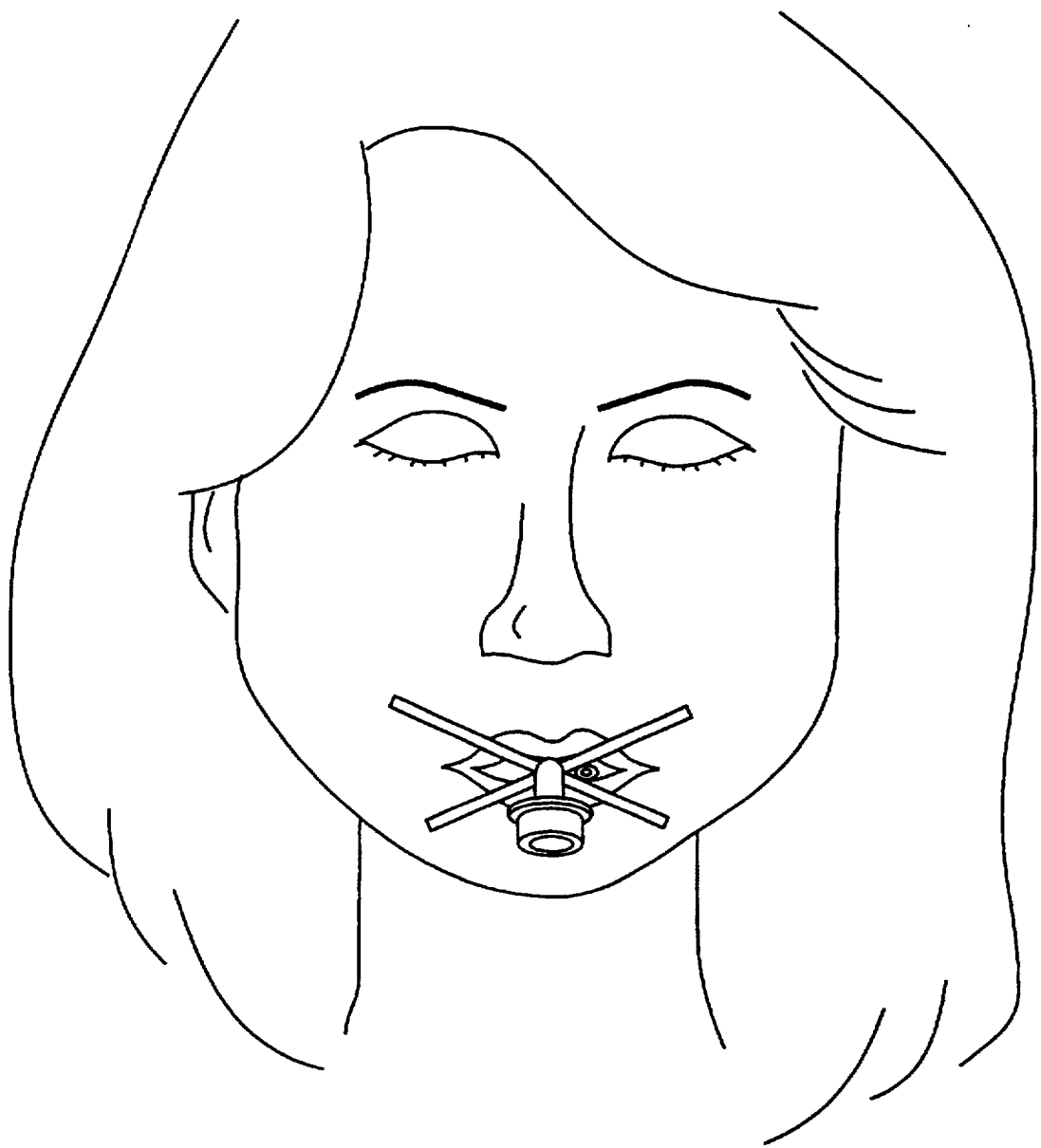
FIG. 6 is a plan view of an endotracheal tube with a Guedel oral airway conventionally applied to patient with adhesive tapes.

Employing those adhesive backed holding wings 11, 12 to fasten the endotracheal tube holder to the patient for short term applications, or using a double Y-ended elastic/plain strap 60 by connecting the strap to the holding holes 112, 122 and go around the patient's neck for prolong application, or for whose who has beard, or oily or hairy skin (as shown in FIG. 2B). A plurality of accessory fastening means, such as I-shaped and H-shaped straps 80, 90 showing in FIGS. 4A and 4B are for special clinical situations. As shown in FIGS. 2A and 4A, the endotracheal tube holder is secured to the patient by using the I-shaped strap 80 with other holding wing being cut off to facilitate mouth opening. The elastic/plain strap 60 can be connected to the holding holes 112, 122 at the ends for further reinforcement for prolong application or for those who has beard, or oily or hairy skin.

Figure 3:
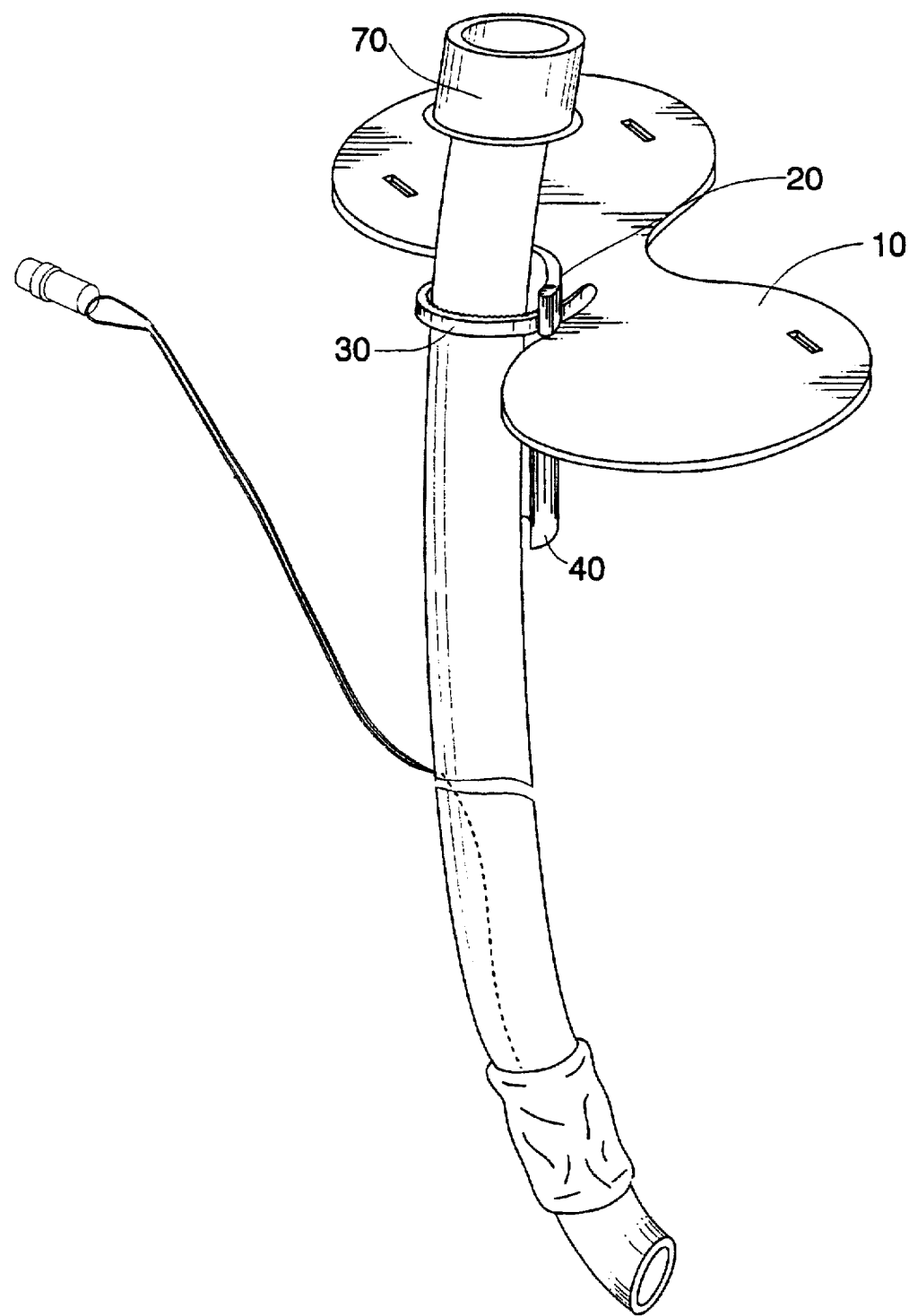
FIG. 3 is a perspective view of the above embodiment with an endotracheal tube firmly holding in position according to the present invention.

Referring to FIGS. 1 to 3, in order to secure the endotracheal tube 70 firmly and fast, the inner aspect side of the tube securing element 20 and that of the bite block 40 both form a longitudinal concave tube recess 21 and 41 respectively. Each of the recesses 21, 41 has a curvature conformed to the concave curvature 111 of the central neck 13 of the holding element 10, so that the endotracheal tube 70 can be abutted upon the tube recesses 21 and 41 longitudinally as shown in FIG. 3.

The tube securing element 20 further comprises a securing means for holding the endotracheal tube 70 firmly and to prevent the tube from dislodging or displacement. The securing means comprises a holding strap 30 extended transversely from one longitudinal side of the tube securing element 20, and a locking strap slot 22 provided at the other longitudinal side of the tube securing element 20. The locking strap slot 22 has a width slightly less than the thickness of the holding strap 30 for securing the holding strap 30. The strap slot 22 has a top opening and a reverse tooth so as to provide an elastic spring-like feature for engaging with the holding strap 30 more easily.

Accordingly, with the tube securing element 20 positioned upward and the tube recesses 21, 41 facing towards the endotracheal tube 70, the endotracheal tube 70 can be secured to the tube securing element 20 by encircling the holding strap 30 around the endotracheal tube 70 and then sliding the holding strap 30 down through the locking strap slot 22 and by pulling the holding strap 30 tight to hold the endotracheal tube 70 firmly in position with the tube securing element 20. The inner aspect side of the holding strap 30 has a plurality of coordinating holding teeth 31 protruded thereon so as to engage with the outer surface of the endotracheal tube 70 in order to increase the relative surface friction for preventing tube sliding and to ensure better securing effect with the locking strap slot 22.

When the endotracheal tube 70 needs to be repositioned, loosen the endotracheal tube 70 by twisting the upper edge of the holding strap 30 outward and by sliding it upward from the locking strap slot 22. Adjust the endotracheal tube 70 position and using stethoscope ausculatation of breath sounds or radiological examinations to confirm the position of the tip of the repositioned endotracheal tube 70. Then secure the endotracheal tube 70 in a new position without loosing and resecuring the whole device.

Referring to FIG. 2B, the endotracheal tube 70 is secured to the patient by connecting the double Y-ended elastic/plain strap 60 to the holding holes 112, 122 on the holding wings 11, 12 and go around the patient's neck for prolong application or for those who has beard, or oily or hairy skin.

As shown in FIG. 3, the relationships of the tube securing element 20 and the bite-block 40 of the present invention to the endotracheal tube 70 in use is illustrated. The bite-block 40 is closely secured to the endotracheal tube 70, and due to the firm quality and its straight shape, it can protect the endotracheal tube 70 from patient's biting in any clinical situation.

All above mentioned elements being manufactured in various sizes according to patient's age from newborn to adult with non-toxic plastic materials. They are of miniature sizes in order to facilitate handling, patient care procedures and to minimize tissue trauma, as well as to provide a low cost construction suitable economically to permit an one-time use that would also prevent contamination between patients and/or healthcare personnel.

The equipment and procedure as described have many advantages over other devices and methods. Advantages include fast and easy of operation, firm fasten of the endotracheal tube to the patient, thus preventing dislodgment, displacement of the tube, accidental extubation and patient's biting on the tube. The build in bite-block causes less obstruction of mouth cavity, minimal risk of trauma and subsequently infection to the oropharyngeal tissues.

Endotracheal intubation and subsequently adequate ventilation and oxygen supply as previously discussed is often employed as a life-saving technique in modern medical practice. If the endotracheal tube is not properly secured and protected, it may result in loss of airway and endanger patient's life. Current method of securing endotracheal tube by ordinary medical adhesive tapes and employing an oral airway to prevent patient biting is not only inefficient but also may cause complications by the equipments themselves. This dual function endotracheal tube holder with integrated bite-block provides means to firmly secure the endotracheal tube in place and and to prevent patient's biting on the tube, thus, avoiding the most serious complications of endotracheal intubation and subsequently improvement of patient safety.

I claim:

1. An endotracheal tube holder for holding an endotracheal tube to a patient, comprising:

a holding element, which comprises a central neck and two holding wings integrally extended from two ends of said neck respectively for fast and firmly fastening to a patient, wherein each of said two holding wings is in enlarged circular disc shape and two transverse side edges of said central neck form two opposing concave curvatures respectively to facilitate intro-oral observation, manipulaton and suctioning, and that each of said holding wings has two holding holes respectively formed on two opposing outer sides thereof;

a tube securing element comprising a securing element which is a protrusion having a predetermined height integrally and perpendicularly protruded from one side of said central neck of said holding element for accommodating an endotracheal tube thereto for firmly securing such an endotracheal tube in position for preventing such an endotracheal tube from dislodging and displacement, an inner aspect side of said tube securing element forms a longitudinal concave tube recess which has a curvature conformed to one of said concave curvatures of said central neck of said holding element, wherein said tube securing means further comprises a holding strap extended transversely from one longitudinal side of said tube securing element, and that a locking strap slot is provided at another longitudinal side of said tube securing element which has a width slightly smaller than a thickness of said holding strap to provide an elastic resilient feature for engaging with said holding strap for firmly securing with said holding strap, wherein said strap slot has a top opening and a reverse tooth for providing an elastic resilient feature for easily and firmly engaging with said holding strap, an inner aspect side of said holding strap having a plurality of coordinating holding teeth protruded thereon so as to engage with an outer surface of said endotracheal tube in order to increase a relative surface friction therebetween for preventing tube sliding and ensuring better securing effect with said locking strap slot, whereby positioning said tube securing element in a position in which said tube securing element faces towards such an endotracheal tube, such an endotracheal tube being secured to such an endotracheal tube holder by encircling said holding strap around such an endotracheal tube and then sliding said holding strap down through said locking strap slot and by pulling said holding strap tight to firmly hold such an endotracheal tube in position;

an intra-oral means which comprises an elongated bite-block integrally extended longitudinally from the other side of said neck of said holding element, for inserting into a patient's mouth to prevent a patient from biting on such an endotracheal tube, wherein an inner aspect side of said bite-block also forms a longitudinal concave tube recess which also has a curvature conformed to one of said concave curvature of said central neck of said holding element, therefore such an endotracheal tube is capable of abutting upon said tube recesses of said tube securing element and said bite-block longitudinally; and a fastening means for firmly fastening said endotracheal tube holder to a patient, wherein said fastening means is a double Y-ended strap having two Y-shaped ends each connected with said two holding holes provided on each of said two holding wings respectively so as to go around a patient's neck.

2. An endotracheal tube holder for holding an endotracheal tube to a patient, comprising:

a holding element, which comprises a central neck and two holding wings integrally extended from two ends of said neck respectively for fast and firmly fastening to a patient, wherein each of said two holding wings is in enlarged circular disc shape and two transverse side edges of said central neck form two opposing concave curvatures respectively to facilitate intro-oral observation, manipulaton and suctioning, and that each of said holding wings has two holding holes respectively formed on two opposing outer sides thereof;

a tube securing element comprising a securing element which is a protrusion having a predetermined height integrally and perpendicularly protruded from one side of said central neck of said holding element for accommodating such an endotracheal tube thereto for firmly securing such an endotracheal tube in position for preventing such an endotracheal tube from dislodging and displacement, an inner aspect side of said tube securing element forms a longitudinal concave tube recess which has a curvature conformed to one of said concave curvatures of said central neck of said holding element, wherein said tube securing means further comprises a holding strap extended transversely from one longitudinal side of said tube securing element, and that a locking strap slot is provided at another longitudinal side of said tube securing element which has a width slightly smaller than a thickness of said holding strap to provide an elastic resilient feature for engaging with said holding strap for firmly securing with said holding strap, wherein said strap slot has a top opening and a reverse tooth for providing an elastic resilient feature for easily and firmly engaging with said holding strap, an inner aspect side of said holding strap having a plurality of coordinating holding teeth protruded thereon so as to engage with an outer surface of such an endotracheal tube in order to increase a relative surface friction therebetween for preventing tube sliding and ensuring better securing effect with said locking strap slot, whereby positioning said tube securing element in a position in which said tube securing element faces towards such an endotracheal tube, such an endotracheal tube being secured to said endotracheal tube holder by encircling said holding strap around said endotracheal tube and then sliding said holding strap down through said locking strap slot and by pulling said holding strap tight to firmly hold such an endotracheal tube in position;

an intra-oral means which comprises an elongated bite-block integrally extended longitudinally from the other side of said neck of said holding element, for inserting into a patient's mouth to prevent patient from biting on such an endotracheal tube, wherein an inner aspect side of said bite-block also forms a longitudinal concave tube recess which also has a curvature conformed to said concave curvature of said central neck of said holding element, therefore such an endotracheal tube is capable of abutting upon said tube recesses of said tube securing element and said bite-block longitudinally; and a fastening means which comprises an elastic strap connected to said holding element for going around a neck of a patient, wherein said elastic strap is a H-shaped elastic strap for connecting with said two holding wings through said two holding holes respectively provided on said two holding wings.

* * * * *